United States Patent
Chen

(10) Patent No.: US 11,013,372 B2
(45) Date of Patent: May 25, 2021

(54) TAKE-OUT FOOD CASE FOR KEEPING FOOD FRESH

(71) Applicant: DONGGUAN UNIVERSITY OF TECHNOLOGY, Guangdong (CN)

(72) Inventor: Baiman Chen, Guangdong (CN)

(73) Assignee: DONGGUAN UNIVERSITY OF TECHNOLOGY, Dongguan (CN)

( * ) Notice: Subject to any disclaimer, the term of this patent is extended or adjusted under 35 U.S.C. 154(b) by 302 days.

(21) Appl. No.: 16/149,163

(22) Filed: Oct. 2, 2018

(65) Prior Publication Data

US 2019/0290074 A1 Sep. 26, 2019

(30) Foreign Application Priority Data

Mar. 23, 2018 (CN) .......................... 201810246716.8

(51) Int. Cl.
*A47J 47/14* (2006.01)
*A47J 41/00* (2006.01)
*A61L 2/10* (2006.01)
*A61L 2/26* (2006.01)
*B65D 81/38* (2006.01)

(52) U.S. Cl.
CPC ........... *A47J 47/14* (2013.01); *A47J 41/0094* (2013.01); *A61L 2/10* (2013.01); *A61L 2/26* (2013.01); *B65D 81/3813* (2013.01); *A61L 2202/11* (2013.01); *A61L 2202/23* (2013.01)

(58) Field of Classification Search
CPC ... A47J 41/0094; A47J 47/14; A61L 2202/11; A61L 2202/122; A61L 2202/23; A61L 2/10; A61L 2/24; A61L 2/26; B65D 81/3813; H05B 3/145; H05B 3/42

USPC .......................................................... 219/387
See application file for complete search history.

(56) References Cited

U.S. PATENT DOCUMENTS

| 1,903,169 | A | * | 3/1933 | Cordrey | .................... | F17C 3/10 |
| | | | | | | 220/560.14 |
| 5,535,888 | A | * | 7/1996 | De Luca | ............. | B65D 81/052 |
| | | | | | | 206/521 |
| 8,980,188 | B2 | * | 3/2015 | Park | ...................... | F25D 17/042 |
| | | | | | | 422/186 |

FOREIGN PATENT DOCUMENTS

| CN | 105876068 | * | 8/2016 |
| CN | 206247737 | * | 6/2017 |

* cited by examiner

*Primary Examiner* — Dana Ross
*Assistant Examiner* — Joseph W Iskra

(57) ABSTRACT

The present invention relates to the field of take-out food cases, more particularly to a take-out food case for keeping food fresh. The principle is as follows. The temperature information of the heat insulation portion is detected and fed back to the temperature controller by the thermocouple probe. When the detected temperature is lower than the minimum temperature preset by the temperature controller, carbon fiber heating pipes are controlled to heat the food by the temperature controller. When the temperature inside the heat insulation portion reaches to the maximum temperature preset by the temperature controller, carbon fiber heating pipes are controlled to stop heating by means of the temperature controller. When the take-out food case for keeping food fresh is not in use, ultraviolet sterilizing lamps are controlled to perform regular sterilization for the take-out food case by means of the timer.

6 Claims, 3 Drawing Sheets

TAKE-OUT FOOD CASE FOR KEEPING FOOD FRESH

CROSS-REFERENCE TO PRIOR APPLICATION

This application claims the benefit of Chinese Patent Application No. 201810246716.8 filed on Mar. 23, 2018, the contents of which are incorporated herein by reference.

FIELD OF THE INVENTION

The present invention relates to the field of take-out food cases, more particularly to a take-out food case for keeping food fresh.

BACKGROUND OF THE INVENTION

With the continuous development of the society, pace of modern life accelerates, and various new industries such as take-out food industry are generated in such fast-paced life. As the popularization of the telephone, the mobile phone and the Internet, the take-out food industry develops rapidly. Nowadays, convenient take-out food is more and more popular, and it is desirable to overcome its drawbacks. It is found that existing take-out food cases for containing the take-out food do not have sterilization function or heat and cold insulation function, as a result of which the take-out food can hardly be kept fresh.

It is reported that many restaurants never sterilize the take-out food cases even after long periods of use, and apparently the sanitary condition of the take-out food cases is bad. It is known that, during the food delivery, sometimes the deliverymen may accidently spill some soup on the take-out food cases. However, many deliverymen merely clean it up with tissues, leaving the bacteria to grow in the take-out food cases to contaminate the food and do harm to human health. Moreover, in order to keep food warm or cold, some deliverymen put insanitary towels under or over the food inside the take-out food cases. In these cases, the take-out food that the customer receives not only become cold meals or unfrozen drinks, but also is contaminated and unclean.

Furthermore, since existing take-out boxes cannot absorb water vapor, the water vapor evaporated from the food condenses into water, stays in the box and mixes with the food, which makes the food taste worse. All the above problems affect the food taste, lead to customers' negative evaluations for the take-out food, and impact the reputation of restaurants.

SUMMARY OF THE INVENTION

The present invention aims to provide an improved take-out food case to solve the above problems of existing take-out food cases.

A take-out food case for keeping food fresh comprises a case body and a case cover, the case body comprises a heat insulation portion and a cold insulation portion, the heat insulation portion of the case body and the case cover are respectively provided with a wire hole and the wire holes are in communication with each other, four first seal grooves are arranged at four corners inside the heat insulation portion, and the first seal grooves are respectively inserted with a sealing strip, a plurality of circular cavities are evenly provided along a centre line of each sealing strip, a carbon fiber heating pipe is arranged between corresponding circular cavities of two adjacent sealing strips, each sealing strip is arranged at one side with a sealing ridge which matches with respective first seal groove and at another side with two second seal grooves which form an angle of 90 degrees therebetween, a perforated baffle is arranged in opposite second seal grooves of two adjacent sealing strips, and the perforated baffle is arranged at a central part with a first protrusion which holds a layered perforated baffle, the layered perforated baffle is arranged with a fixing groove which matches with a take-out box and the take-out box is disposed on the fixing groove, an ultraviolet sterilizing lamp is arranged in the case cover, a control system is arranged on an outer surface of the case cover, the control system comprises an internal power supply, a temperature controller, a timer and a displayer, a thermocouple probe is further arranged inside the heat insulation portion, and the control system is connected with the thermocouple probe, the ultraviolet sterilizing lamp and the carbon fiber heating pipe by a wire which passes through the wire holes.

In a further embodiment of the present invention, a vertical groove is arranged on an inner wall of the cold insulation portion, and the vertical groove is inserted with the perforated baffle.

In a further embodiment of the present invention, a second baffle is arranged in the case cover, ultraviolet sterilizing lamps are arranged respectively at two sides of the second baffle in the case cover, fixed barriers are arranged at two sides below the ultraviolet sterilizing lamps. The fixed barriers are arranged at two ends with recesses, in which movable barriers are arranged. The movable barriers are movable such that when the movable barriers are open, the ultraviolet sterilizing lamps are capable of radiating ultraviolet to the heat insulation portion and the cold insulation portion, so as to sterilize the heat insulation portion and the cold insulation portion.

In a further embodiment of the present invention, a first baffle is arranged between the heat insulation portion and the cold insulation portion, and the first baffle is arranged with a baffle groove. The second baffle and the first baffle are arranged opposite to each other, and both are made of thermal insulation materials. The second baffle is provided with a protruding portion, which protruding portion matches with the baffle groove so as to achieve sealing of the heat insulation portion and the cold insulation portion.

In a further embodiment of the present invention, movable barriers are arranged with second protrusions for facilitating manual gripping to move the movable barriers.

In a further embodiment of the present invention, a cover of the take-out box is made of materials which are capable of absorbing moisture, so as to absorb the water vapor evaporated from the food.

In a further embodiment of the present invention, the control system is powered by a rechargeable battery, and a charging port which is electrically connected with the rechargeable battery is arranged on a side surface of the case body or the case cover. The charging port can be connected to a power source of an electric vehicle via a power line, so as to allow the power source of the electric vehicle to charge the rechargeable battery and/or directly supply power for the control system.

In a further embodiment of the present invention, when the power source of the electric vehicle charges the rechargeable battery and/or directly supplies power for the control system, the ultraviolet sterilizing lamp is turned on and controlled by the control system to perform sterilization.

In a further embodiment of the present invention, the case body and the case cover are respectively arranged with a solar panel, the solar panels are electrically connected with the control system, such that when the solar panels are available for powering, an internal power source of the control system cuts off power supply to stop the use of the internal power source of the control system.

In a further embodiment of the present invention, a temperature indicating recorder label, which is capable of changing colors as the temperature of the take-out box changes or displaying temperature values, is attached on a surface of the take-out box.

In a further embodiment of the present invention, the layered perforated baffle is arranged with a fan which is electrically connected with the control system and used for maintaining air circulation inside the take-out food case.

The present invention has advantages as follows. Due to the thermocouple probe arranged in the heat insulation portion, when the temperature of the heat insulation portion detected by the thermocouple probe is lower than a predetermined value, the carbon fiber heating pipe is controlled to heat the food inside the heat insulation portion by means of the temperature controller. Furthermore, inside the take-out food case an ultraviolet sterilizing lamp is arranged so as to allow the sterilization of the take-out food case.

BRIEF DESCRIPTION OF THE DRAWINGS

In order to illustrate the technical solution of the invention or prior art more clearly, drawings of the embodiments or prior art are briefly described below. Apparently, the described drawings merely illustrate some embodiments of the invention. Other drawings can be derived from these drawings by those skilled in the art without any inventive step.

DETAILED DESCRIPTION OF ILLUSTRATED EMBODIMENTS

In order to make objects, features and advantages of the present invention more clear and facilitate understanding of the present invention, the technical solutions according to the embodiments of the present invention are clearly and fully described below in conjunction with drawings of the embodiments. Apparently, the described embodiments are merely some embodiments of the invention, but not all embodiments. Based on the embodiments of the present invention, all the other embodiments achieved by those skilled in the art without any inventive step fall within the scope of the present invention.

The technical solutions of the present invention will be further explained below in conjunction with figures and particular embodiments.

Figure 1:
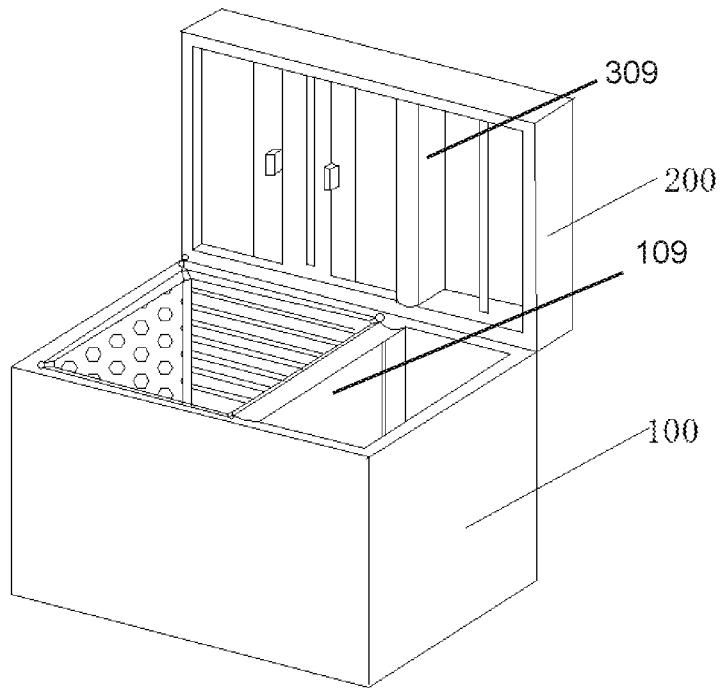
FIG. 1 is a schematic drawing showing an overall structure of a take-out food case according to an embodiment of the present invention.
Figure 2:
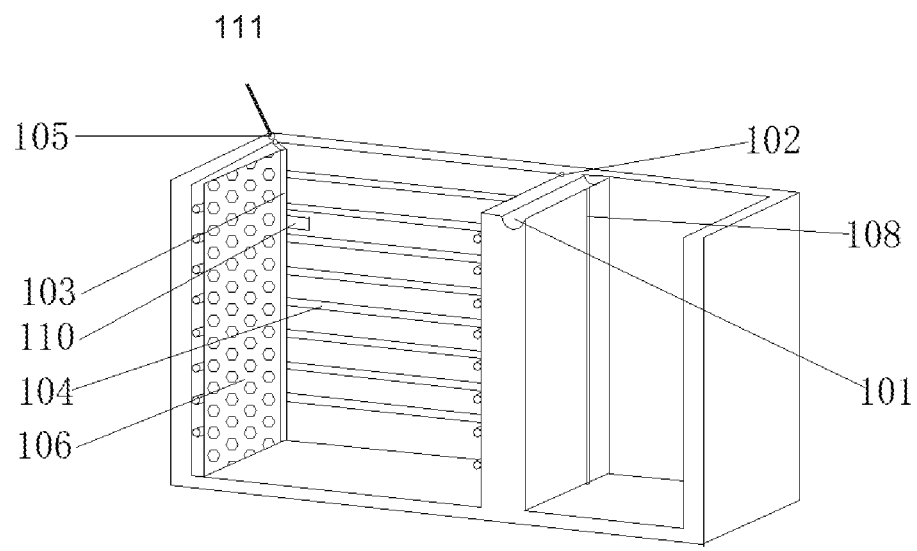
FIG. 2 is an axonometric drawing of a case body of a take-out food case according to an embodiment of the present invention.
Figure 3:
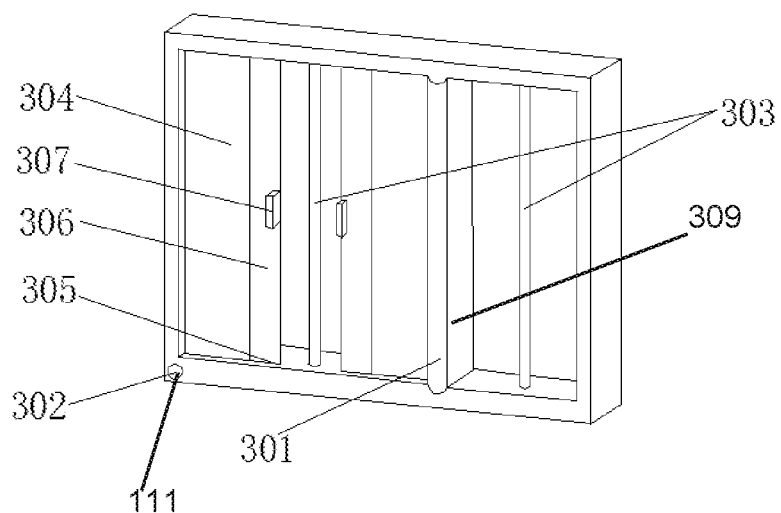
FIG. 3 is a schematic drawing showing an internal structure of a case cover of a take-out food case according to an embodiment of the present invention.
Figure 4:
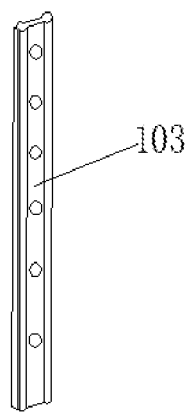
FIG. 4 is a schematic drawing showing an overall structure of a sealing strip of a take-out food case according to an embodiment of the present invention.
Figure 5:
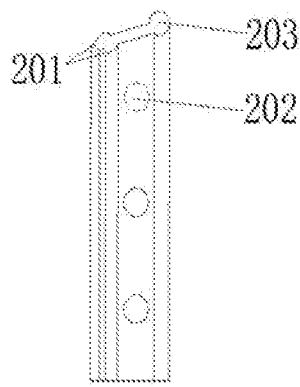
FIG. 5 is a partially schematic drawing of a sealing strip of a take-out food case according to an embodiment of the present invention.
Figure 6:
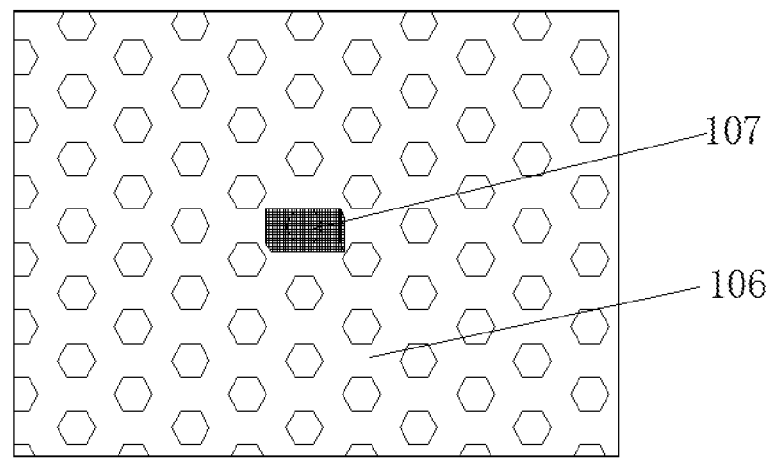
FIG. 6 is a schematic drawing of a perforated baffle of a take-out food case according to an embodiment of the present invention.
Figure 7:
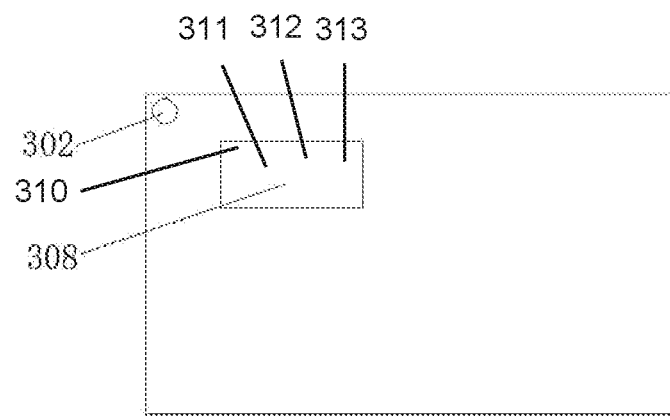
FIG. 7 is a schematic drawing showing an outer surface of a case cover of a take-out food case according to an embodiment of the present invention.
Figure 8:
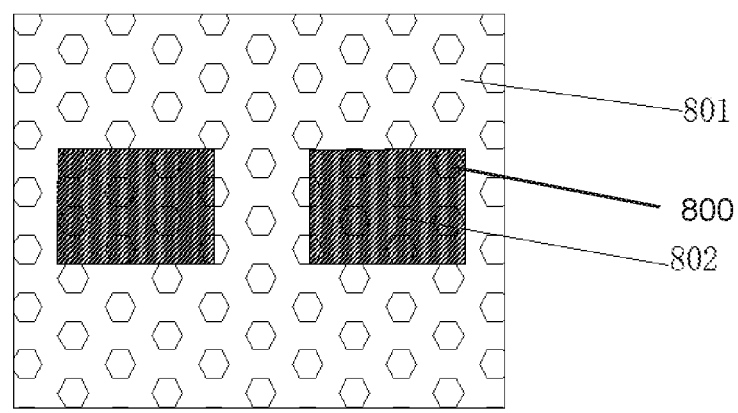
FIG. 8 is a schematic drawing of a layered perforated baffle of a take-out food case according to an embodiment of the present invention.

Referring to FIGS. 1-8, a take-out food case for keeping food fresh according to an embodiment of the present invention comprises a case body 100 and a case cover 200, the case body comprises a heat insulation portion and a cold insulation portion, a wire hole 105 and a wire hole 302 are respectively provided in the heat insulation portion of the case body and in the case cover and are in communication with each other. Four first seal grooves 102 are arranged at four corners inside the heat insulation portion, and the first seal grooves are respectively inserted with sealing strips 103, a plurality of circular cavities 202 are arranged along a centre line of each sealing strip. Carbon fiber heating pipes 104 are arranged between corresponding circular cavities of two adjacent sealing strips. Each of the sealing strips is arranged at one side with a sealing ridge 203 which matches with respective first seal groove and at another side with two second seal grooves 201 which form an angle of 90 degrees therebetween. Perforated baffles 106 are arranged between opposite second seal grooves of two adjacent sealing strips, and each perforated baffle is arranged at a central part with a first protrusion 107 which holds a layered perforated baffle 801. The layered perforated baffle is arranged with a fixing groove 802 which matches with a take-out box 800, and the take-out box 800 is held at the fixing groove. Ultraviolet sterilizing lamps 303 are arranged in the case cover 200. A control system is arranged on the outer surface of the case cover 200. The control system 308 comprises an internal power supply 310, a temperature controller 311, a timer 312, and a displayer 313. A thermocouple probe 110 is further arranged inside the heat insulation portion. The control system 308 is connected with the thermocouple probe 110, the ultraviolet sterilizing lamps 303, and the carbon fiber heating pipes 104 by a wire 111 which passes through the wire holes 105, 302. Herein, the internal power supply is used for supplying power to the thermocouple probe 110, the ultraviolet sterilizing lamps 303, and the carbon fiber heating pipes 104.

According to the invention, vertical grooves 108 are arranged on the inner wall of the cold insulation portion, and the vertical grooves can be inserted with perforated baffles 106.

According to the invention, a second baffle is arranged in the case cover, ultraviolet sterilizing lamps 303 are arranged respectively at two sides of the second baffle in the case cover, fixed barriers 304 are arranged at two sides below the ultraviolet sterilizing lamps 303. The fixed barriers 304 are arranged at two ends with recesses 305, in which movable barriers 306 are arranged. The movable barriers 306 are movable such that when the movable barriers are open, the ultraviolet sterilizing lamps 303 are capable of radiating ultraviolet to the heat insulation portion and the cold insulation portion, so as to sterilize the heat insulation portion and the cold insulation portion.

According to the invention, a first baffle 109 is arranged between the heat insulation portion and the cold insulation portion, and is arranged with a baffle groove 101. The second baffle 309 and the first baffle 109 are arranged opposite one another, and both are made of thermal insulation materials. The second baffle 309 is provided with a protruding portion 301, which protruding portion matches with the baffle groove so as to achieve sealing of the heat insulation portion and the cold insulation portion.

According to the invention, movable barriers are arranged with second protrusions 307 for facilitating manual gripping to move the movable barriers 306.

According to the invention, a cover of the take-out box is made of materials which are capable of absorbing moisture, so as to absorb the water vapor evaporated from the food.

According to the invention, the control system is powered by a rechargeable battery (i.e. the internal power supply is a rechargeable battery), and a charging port which is electrically connected with the rechargeable battery is arranged on a side surface of the case body or the case cover. The charging port can be connected to a power source of an electric vehicle via a power line, so as to allow the power source of the electric vehicle to charge the rechargeable battery and/or directly supply power for the control system.

According to the invention, when the power source of the electric vehicle charges the rechargeable battery and/or supplies power for the control system directly, the ultraviolet sterilizing lamps are turned on and controlled by the control system to perform sterilization.

According to the invention, the case body and the case cover are arranged with solar panels which are electrically connected with the control system. When the solar panels are available for powering, the internal power source of the control system cuts off the power supply, to stop the use of the internal power source of the control system.

According to the invention, a temperature indicating recorder label, which changes colors as the temperature of the take-out box 800 changes or displays the temperature values, is attached on the surface of the take-out box 800.

According to the invention, the layered perforated baffle is arranged with a fan, and the fan is electrically connected with the control system so as to maintain air circulation inside the take-out food case.

The principle of the invention is as follows. The temperature information of the heat insulation portion is detected and fed back to the temperature controller by means of the thermocouple probe. When the temperature detected by the thermocouple probe is lower than the minimum temperature preset by the temperature controller, carbon fiber heating pipes are controlled to heat the food inside the heat insulation portion by means of the temperature controller. When the temperature inside the heat insulation portion reaches to the maximum temperature preset by the temperature controller, carbon fiber heating pipes are controlled to stop heating by means of the temperature controller. When the take-out food case for keeping food fresh is not in use, ultraviolet sterilizing lamps are controlled to perform regular sterilization for the take-out food case by means of the timer.

All the above are merely preferred embodiments of the present invention, but are not to limit the invention in any form. The present invention is intended to cover all changes, various modifications and equivalent arrangements included within the principle and scope of the present invention.

The invention claimed is:

1. A take-out food case for keeping food fresh, characterized in that, it comprises a case body and a case cover, wherein the case body comprises a heat insulation portion and a cold insulation portion, the heat insulation portion of the case body and the case cover are respectively provided with a wire hole for allowing a wire to pass though, four first seal grooves are arranged at four corners inside the heat insulation portion, and the first seal grooves are respectively inserted with a sealing strip, a plurality of circular cavities are evenly provided along a centre line of each sealing strip, a carbon fiber heating pipe is horizontally arranged between each two corresponding circular cavities of each two adjacent sealing strips, wherein one side of each sealing strip is arranged with a sealing ridge which matches with respective one of the four first seal grooves and another side of each sealing strip is arranged with two second seal grooves, the two second seal grooves form an angle of 90 degrees therebetween, a perforated baffle is arranged between opposite second seal grooves of two adjacent sealing strips, and a central part of the perforated baffle is arranged with a first protrusion, and a layered perforated baffle is disposed on and held by the first protrusion, the layered perforated baffle is arranged with a fixing groove which matches with a take-out box, and the take-out box is disposed in the fixing groove, wherein in the case cover an ultraviolet sterilizing lamp is arranged, and on an outer surface of the case cover a control system is arranged, wherein the control system comprises an internal power supply, a temperature controller, a timer and a displayer, a thermocouple probe is further arranged inside the heat insulation portion, and the control system is connected with the thermocouple probe, the ultraviolet sterilizing lamp and the carbon fiber heating pipe by a wire which passes through the wire holes.

2. The take-out food case for keeping food fresh according to claim 1, characterized in that, a vertical groove is arranged on an inner wall of the cold insulation portion, and the vertical groove is inserted with the perforated baffle.

3. The take-out food case for keeping food fresh according to claim 1, characterized in that, a second baffle is arranged in the case cover, ultraviolet sterilizing lamps are arranged respectively at two sides of the second baffle in the case cover, and fixed barriers are arranged respectively at two sides below the ultraviolet sterilizing lamps, wherein the fixed barriers are arranged at two ends with recesses, in which movable barriers are arranged, wherein the movable barriers are movable such that when the movable barriers are open, the ultraviolet sterilizing lamps are capable of radiating ultraviolet to the heat insulation portion and the cold insulation portion, so as to sterilize the heat insulation portion and the cold insulation portion.

4. The take-out food case for keeping food fresh according to claim 3, characterized in that, a first baffle is arranged between the heat insulation portion and the cold insulation portion, and the first baffle is arranged with a baffle groove, wherein the second baffle and the first baffle are arranged opposite to each other, and both are made of thermal insulation materials, wherein the second baffle is provided with a protruding portion, which protruding portion matches with the baffle groove so as to achieve sealing of the heat insulation portion and the cold insulation portion.

5. The take-out food case for keeping food fresh according to claim 3, characterized in that, movable barriers are arranged with second protrusions for facilitating manual gripping to move the movable barriers.

6. The take-out food case for keeping food fresh according to claim 1, characterized in that, a cover of the take-out box is made of a material which is capable of absorbing moisture, so as to absorb water vapor evaporated from the food.

* * * * *